(12) United States Patent
Maierhofer et al.

(10) Patent No.: US 10,155,077 B2
(45) Date of Patent: Dec. 18, 2018

(54) DIALYSIS MACHINE, AND METHOD OF DETERMINING THE CALCIFICATION IN A DIALYSIS MACHINE

(71) Applicants: Fresenius Medical Care Deutschland GmbH, Bad Homburg (DE); Christiane Koch, Gerolzhofen (DE)

(72) Inventors: Andreas Maierhofer, Schweinfurt (DE); Alfred Gagel, Litzendorf (DE); Malte Gross, Niederwerrn (DE); Michael Koch, Gerolzhofen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 338 days.

(21) Appl. No.: 14/542,947

(22) Filed: Nov. 17, 2014

(65) Prior Publication Data

US 2015/0136702 A1    May 21, 2015

Related U.S. Application Data

(63) Continuation of application No. 12/448,979, filed as application No. PCT/EP2008/000339 on Jan. 17, 2008, now abandoned.

(30) Foreign Application Priority Data

Jan. 26, 2007 (DE) .................. 10 2007 004 115

(51) Int. Cl.
    *A61M 1/16* (2006.01)
(52) U.S. Cl.
    CPC ............ *A61M 1/1605* (2014.02); *A61M 1/16* (2013.01); *A61M 1/165* (2014.02); *A61M 1/1607* (2014.02); *A61M 1/1609* (2014.02); *A61M 1/169* (2013.01); *A61M 2205/3317* (2013.01); *A61M 2205/3324* (2013.01); *A61M 2205/3327* (2013.01); *A61M 2205/702* (2013.01);
    (Continued)

(58) Field of Classification Search
    None
    See application file for complete search history.

(56) References Cited

U.S. PATENT DOCUMENTS

| 4,508,622 | A | 4/1985 | Polaschegg et al. |
| 5,326,476 | A | 7/1994 | Grogan et al. |

(Continued)

FOREIGN PATENT DOCUMENTS

| DE | 3223051 | 12/1983 |
| DE | 10114283 | 7/2002 |

(Continued)

*Primary Examiner* — Krishnan S Menon
(74) *Attorney, Agent, or Firm* — Kilyk & Bowersox, P.L.L.C.

(57) ABSTRACT

A dialysis machine has at least one filter for the filtration of dialysis liquid and a device for determining calcification of the dialysis machine. The device has one or more sensors configured and arranged to detect either downstream, or upstream and downstream, of the at least one filter an ion concentration or a parameter representative of the ion concentration or of its change of the dialysis liquid, of a solution serving the decalcification or of another measuring solution. The device for determining the calcification of the dialysis machine has an evaluation or calcification unit configured to determine the calcification of the dialysis machine based on the ion concentration or parameter value detected by the sensor or sensors.

19 Claims, 8 Drawing Sheets

(52) U.S. Cl.
CPC .............. *A61M 2205/707* (2013.01); *A61M 2205/7554* (2013.01)

(56) References Cited

U.S. PATENT DOCUMENTS

| | | |
|---|---|---|
| 6,080,321 A | 6/2000 | Spickermann |
| 7,563,240 B2 | 7/2009 | Gross et al. |
| 2006/0200064 A1 | 9/2006 | Gross et al. |

FOREIGN PATENT DOCUMENTS

| | | |
|---|---|---|
| DE | 10317024 | 11/2004 |
| EP | 0437274 | 7/1991 |
| EP | 0834328 | 4/1998 |
| GB | 1484642 | 9/1977 |
| WO | WO 01/95956 | 12/2001 |

DIALYSIS MACHINE, AND METHOD OF DETERMINING THE CALCIFICATION IN A DIALYSIS MACHINE

CROSS-REFERENCE TO RELATED APPLICATION

This application is a continuation application of U.S. patent application Ser. No. 12/448,979, filed Jul. 17, 2009, the disclosure of which is incorporated by reference as if fully set forth herein. The aforementioned U.S. patent application Ser. No 12/448,979 is a nationalization of PCT/EP08/000339 filed Jan. 17, 2008 and published in German, which claims priority to DE 10 2007 004 115.4, filed Jan. 26, 2007.

BACKGROUND OF THE INVENTION

1. Field of Invention

The present invention relates to a dialysis machine comprising at least one filter for the filtration of the dialysis liquid and comprising means for determining the calcification of the dialysis machine. The invention further relates to a method of determining the calcification of a dialysis machine.

2. Description of the Prior Art

In the use of dialysis liquids which simultaneously contain high concentrations of calcium ions ($Ca^{2+}$) and bicarbonate ions ($HCO_3^-$), the precipitation of lime ($CaCO_3$) can occur and lime deposits can result in the dialysis machine as a consequence thereof. Under extreme conditions such as, for example, with an additionally low acid content, with long dialysis times or for the case that no decalcifying disinfection is carried out between two dialysis treatments, the said lime deposits can result in failure of the production of dialysis liquid, for example, by blocking of the conveying pumps or by calcification of dialysis liquid filters.

A dialysis machine is known from EP 0 834 328 A1 which comprises means via which an automatic decalcification of the dialysis liquid circuit of the machine can be initiated on the finding of a predetermined degree of calcification of the dialysis machine. Provision can be made in this process for the degree of calcification of the dialysis machine to be able to be determined by clouding of a window of a blood leak detector or by the determination of characteristic parameters of the conveying pump for the dialysis liquid. On the presence of criteria for a decalcification, provision can furthermore be made for the dialysis machine to initiate a decalcification cycle in a fully automatic process.

Whereas the problem of calcification at the machine side, which can result in an abortion of the dialysis and thus in a non-achievement of the treatment goal, is thus generally known, the effects of the lime deposition in the machine on the calcium supply to the patient have previously only been rarely looked at. It is evident that the calcium deposited in the dialysis machine, which is precipitated in the form of lime, can no longer reach the patient. It has been able to be shown in laboratory measurements that the precipitation of $CaCO_3$ can lower the $Ca^{2+}$ ion content at the dialysis-side inlet of the dialyzer to less than 50% of the prescription. This lowering takes place much faster than the failure of the machine due to calcification under specific conditions.

The case can thus occur that the patient is treated with a dialysis liquid for a fairly long time whose $Ca^{2+}$-ion concentration is below the concentration of the ionized calcium in the plasma, which can have the consequence that calcium is removed from the patient in an unwanted manner in the dialysis treatment. The ionized Ca is of great significance with respect to nervous conduction, muscular contraction, myocardial contraction and blood pressure. It can therefore be imagined that negative effects on the patient can occur as a consequence of the machine calcification.

SUMMARY OF THE INVENTION

It is the underlying object of the present invention to further develop a dialysis machine of the initially named kind such that the calcification of the dialysis machine can be recognized reliably before the calcification results in the abortion of the treatment and before the patient is treated with concentrations of calcium ions which are too low over a fairly long period.

This object is satisfied by a dialysis machine having the features described herein. Provision is accordingly made for the machine to have means for determining the calcification of the dialysis machine which comprise one or more sensors, with the sensor or sensors being configured and arranged such that the ion concentration or a parameter of the dialysis liquid representative of the ion concentration or of its change, of a solution serving the decalcification or another measuring solution can be detected upstream or downstream of the filter, The means for determining the calcification of the dialysis machine furthermore comprise an evaluation or calculation unit which is configured such that it determines the calcification of the dialysis machine on the basis of the ion concentration or parameter value detected by means of the sensor or sensors.

The sensor or sensors can, for example, be conductivity sensors, ion-selective electrodes, pH electrodes or sensors working in accordance with spectroscopic processes.

The underlying idea of the invention is that the ion concentration, preferably the $Ca^{2+}$ concentration, or a parameter representative of the ion concentration or of its change, such as the conductivity, are preferably detected downstream, or also upstream and downstream, of the filter or filters and that a conclusion can be made on the calcification of the filter on this basis. In this connection, the ion concentration or the said parameter of the dialysis liquid, of a solution provided for decalcification or of another solution can be detected. This other solution can be an ion-containing solution which, for example, contains $Ca^{2+}$ or $H^+$ ions. Provision can be made in this connection for two sensors to be associated with at least one of the filters, of which one is arranged upstream of the filter and another downstream of the filter. It is conceivable to make the monitoring of the filter or the determination of the degree of calcification of the filter by a comparison of two conductivity measured values, of which one is recorded directly before the filter to be checked and one after the filter to be checked. A calcification of the filter is present when the conductivity value measured upstream of the filter is larger than the conductivity value measured downstream of the filter.

The term of the detection of the "ion concentration of a parameter representative of the ion concentration or of its change" is to be interpreted broadly and comprises, inter alia, also indirect measuring methods for the ion measurement. The measurement of $CO_2$, which is created in the decalcification is, for example, conceivable and covered by the invention. The $CO_2$ concentration is related via the chemical balance to the concentration of other ions and thus forms a measure for the ion concentration so that the measurement of, for example, the $CO_2$ amount, the $CO_2$ concentration or the $CO_2$ volume represents an embodiment of the detection of a parameter representative of the ion concentration.

It is conceivable that a respective sensor is associated upstream and downstream with at least one of the filters both on the primary side of the filter and on the secondary side of the filter. This arrangement makes it possible to detect the calcification of the filter both on the primary side and on the secondary side.

In a further aspect of the invention, provision is made for at least one bypass line to be arranged which can be cut off and which, in the open state, establishes a flow communication of two sensors while bypassing at least one of the filters. If the influence of the filter on the measured values obtained by means of the sensors should be precluded, they are connected to one another in such a manner while bypassing the filter that the dialysis liquid serving the decalcification or a measuring solution first flows through the one and then the other sensor. This makes it possible to be able to compare the measurement values of the sensor with one another or to be able to carry out a calibration of the sensors.

Provision is made in a further aspect of the invention for only one sensor to be provided per filter or for a plurality of filters and for it to be arranged downstream of the filter or filters. A monitoring of the calcification of the filter is thus also possible using one sensor, for example using a conductivity measuring cell which is located downstream of the filter. A determination of the calcification can now take place, for example, in that the conductivity measured value is determined before the start or at the start of the treatment and a check is made during the treatment or also after the treatment as to whether and to what extent a measured value change has occurred.

It is particularly advantageous for at least one bypass line to be provided which can be cut off and which is arranged such that, in the open state, it supplies the dialysis liquid, the solution serving the decalcification or the other measuring solution to the sensor while bypassing at least one filter. It is thus possible also to determine the ion concentration or the parameter representative of this or of its change upstream and downstream of the filter using only one sensor, for example using a conductivity measuring cell arranged downstream of the filter. If the ion concentration or said parameter should be detected upstream of the filter, the bypass line is opened and the solution extracted upstream of the filter by means of the bypass line is supplied to the sensor. The bypass line is closed and the filter is accordingly flowed through for the detection of the measured value on the flowing through of the filter. It is an advantage of this process that only one sensor per filter is needed or also only one sensor is needed for a plurality of filters with associated electronics. In addition, a calibration of a plurality of sensors relative to one another is dispensed with.

The invention furthermore relates to a method of determining the calcification of a dialysis machine, in particular of a dialysis machine as described herein, with the dialysis machine comprising at least one filter for the filtration of the dialysis liquid.

The method is characterized in that the ion concentration or a parameter representative of the ion concentration or of its change of the dialysis liquid or of a solution serving the decalcification or a measuring solution is measured either downstream or upstream and downstream of the filter for the determination of the calcification of the dialysis machine and in that the calcification is determined on the basis of the ion concentration or of the parameter value of the calcification measured. As stated above, the parameter representative of the ion concentration can, for example, be the conductivity, the pH or a parameter determined by means of an ion-selective electrode or by means of spectroscopic processes, such as the absorption or the transmission, for example. The ion concentration is preferably the $Ca^{2+}$ ion concentration or the $H^+$ ion concentration.

Two sensors can be associated with the at least one filter and are arranged downstream and upstream of the filter. The degree of calcification can be determined by a comparison of the ion concentration or of the parameter representative for it or for its change measured upstream and downstream. Provision can be made in this connection for differences in the measured values of the sensors to be determined at a first point in time, preferably before or at the start of a treatment and for these differences then to be taken into account in the determination of the degree of calcification at a second point in time after the first point in time, in particular during the treatment. It is also feasible that the said measured value differences are eliminated by corresponding calibration of the sensors.

In a further aspect of the invention, provision is made for at least one bypass line which can be cut off to be provided which, in the open state, establishes a connection of two sensors while bypassing one of the filters and for the bypass line to be opened for the purpose of determining measured value differences or for calibration of the sensors.

Only one sensor can also be provided per filter or for a plurality of filters and is arranged downstream of the filter or filters, with a measured value being determined at a first point in time, preferably before or at the start of a treatment, by means of the sensor and a check can be made at a second point in time, disposed after the first point in time, in particular during the treatment, whether a measured value change has occurred.

It is also conceivable that only one sensor is provided per filter or for a plurality of filters and is arranged downstream of the filter or filters and that at least one bypass line is provided which can be cut off and which is arranged such that, in the open state, it supplies the dialysis liquid, the solution serving the decalcification or the other measuring solution to the sensor while bypassing at least one filter, with the measured value of the sensor being determined with an open bypass line at the start of or during the treatment and this measured value being compared with the measured value obtained after the flowing through of the filter.

Provision is made in a further aspect of the invention for a decalcification to be carried out and for an evaluation of the decalcification to be carried out after or during the decalcification, said evaluation being based on a comparison of measured values of the one sensor or of the several sensors by means of which the ion concentration or the parameter representative of the ion concentration or of its change is detected upstream and downstream of the filter.

Provision can furthermore be made for an evaluation of the decalcification to be made after the decalcification, said evaluation being based on a comparison of measured values of a sensor before and after the decalcification, with the sensor being arranged downstream of the filter or filters and being configured such that the ion concentration or the parameter representative of it or of its change being detected therewith.

The ion concentration can, for example, be the $Ca^{2+}$ ion concentration or also the $H^+$ ion concentration.

BRIEF DESCRIPTION OF THE DRAWINGS

Further details and advantages of the invention will be explained in more detail with reference to an embodiment shown in the drawing. There are shown.

DETAILED DESCRIPTION OF THE PREFERRED EMBODIMENTS

Further scope of applicability of the present, invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The conductivity of the dialysis liquid is determined by its individual components. The main contribution of the conductivity is due to NaCl, but the $Ca^{2+}$ ions present in relatively low concentrations also contribute to the conductivity. If a dialysis liquid containing both $Ca^{2+}$ and $HCO_3^-$ is in contact with the atmosphere, the outgasing of $CO_2$ results in a consumption of hydrogen carbonate and thus in a pH value shift into the alkaline, which in turn effects a precipitation of calcium carbonate. This is illustrated by the following reaction equation:

$$Ca^{2+}+2HCO_3^- \rightarrow CaCO_3\downarrow+CO_2\uparrow+H_2O$$

Figure 1:
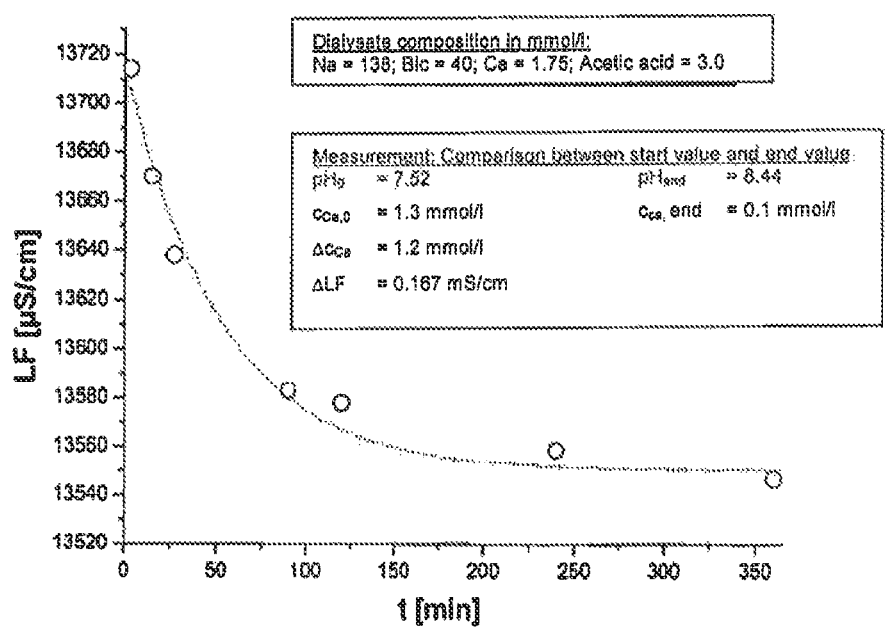
FIG. 1: time curve of the conductivity on Ca precipitation with still dialysis liquid with contact to the atmosphere.

Ions are thus stripped from the dialysis liquid so that the conductivity of the solutions falls. This was able to be demonstrated in lab trials. FIG. 1 shows the drop in conductivity over time with a still dialysis liquid with contact to the atmosphere. As is clearly visible from FIG. 1, the conductivity of the solution falls over time. As can further be seen from the measured values set forth in FIG. 1, this is essentially due to the reduction in the content of calcium ions and, parallel to this, the consumption of hydrogen carbonate ions.

A quantifying of the change in the $Ca^{24}$ ion concentrations in the dialysis liquid is also possible via the change in the conductivity.

Empirical investigations of the influence of the $Ca^{2+}$ ion concentration on the conductivity in typical dialysis liquids produced the following connection:

$$\Delta c = \left(110 \frac{\mu S/cm}{mmol/l}\right)^{-1} \Delta LF$$

With a measuring precision for the conductivity of 10 µS/cm, changes in the $Ca^{2+}$ ion concentration can thus be quantified with an accuracy of 0.1 mmol/l by precipitation of $CaCO_3$.

If, in contrast, the dialysis liquid is generated continuously as fresh using a dialyzer by mixing RO water with an acid component and a bicarbonate containing component, no precipitation is initially to be expected within the short time between the generation and the transport to the dialysis machine.

Figure 2:
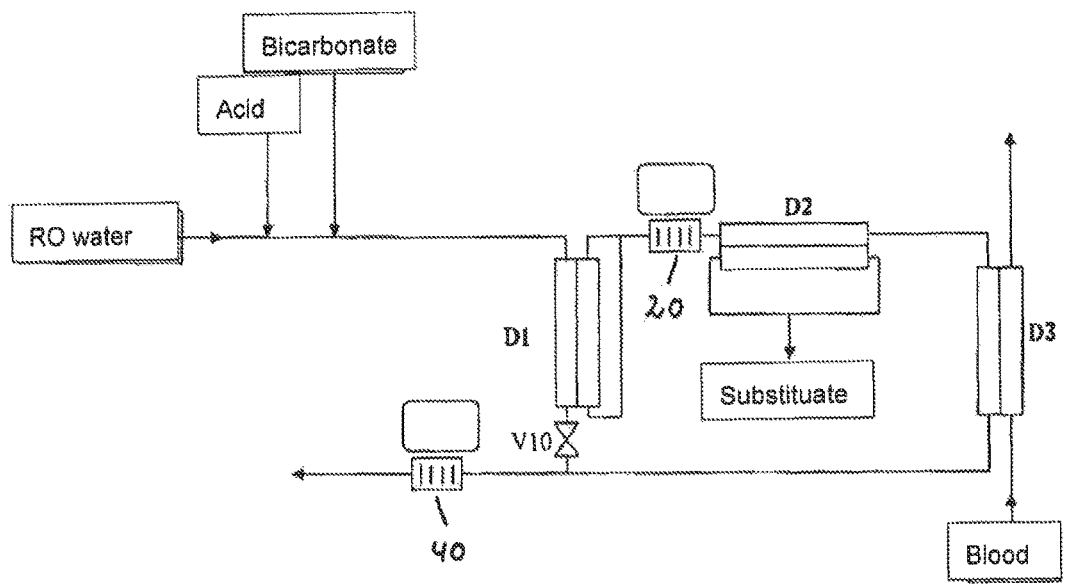
FIG. 2: flow plan of a dialyzer with online preparation of the dialysis liquid.

For the further illustration of the problems of precipitation of $CaCO_3$, reference is initially made to FIG. 2. This Figure shows a flow plan of a dialyzer with online preparation of the dialysate from RO water, acid and bicarbonate. As can be seen from FIG. 2, two sterile filters D1 and D2 are arranged upstream of the dialysis machine D3. In this connection, the sterile filters D1 and D2 are arranged such that the dialysis liquid reaching the dialysis machine D3 moves from the primary side to the secondary side of the first sterile filter D1 and then flows through the primary side of the second sterile filter D2. Substituate is gained in this which is added to the blood of the patient as required, as is the case with hemofiltration and hemodiafiltration. The present invention is naturally not restricted to hemodiafiltration or hemofiltration, but also includes the process of hemodialysis inter alia.

As can further be seen from FIG. 2, a conductivity measuring cell 20 is arranged upstream of the second sterile filter D2 and a second conductivity measuring cell 40 is arranged downstream of the dialysis machine D3 and of the first sterile filter D1.

The conductivity of the dialysis liquid was measured continuously by means of the conductivity of the measuring cell 20.

In addition, the $Na^+$ and $Ca^{2+}$ ion concentration was determined in samples of the dialysis liquid taken directly downstream of the dialysis machine D3.

Figure 3:
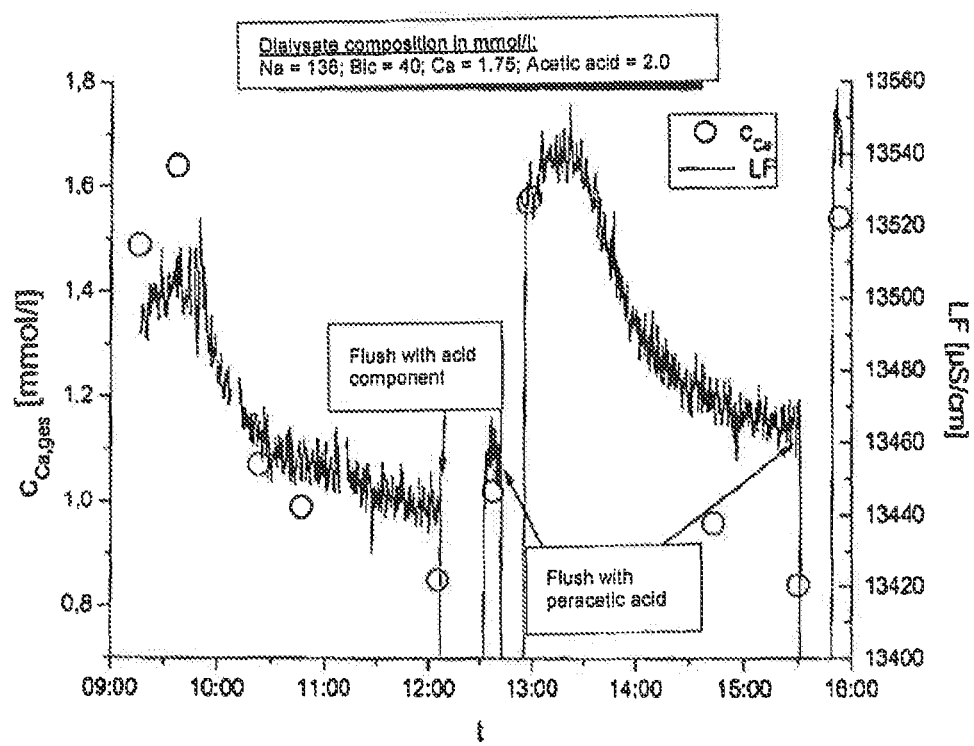
FIG. 3; time curve of the $Ca^{2+}$ ion concentration and of the conductivity during a dialysis treatment with fresh dialysis liquid before and after decalcification.

In FIG. 3, the conductivity measured values (solid line) and the measured values of the Ca ion concentration (circles) are set forth. With a dialysate with a high $Ca^{2+}$ and $HCO_3^-$ content, a clear drop in the $Ca^{2+}$ ion concentration and in the conductivity of the dialysis solution resulted after approximately 2 hours. After intense flushing with a decalcifying cleaning agent, peracetic acid for example, the original $Ca^{2+}$ ion concentrations were again measured, as can be seen from FIG. 3. The conductivity likewise increased again, but with effects by cell drift over time as well as a potential effect of the calcification of the conductivity measuring cell itself having to be taken into account. The $Na^+$ ion concentration remained constant in all cases so that changes in the mixture relationship in the generation of the dialysis liquid can be precluded.

The process shown in FIG. 3 of the drop in conductivity and in the calcium ion concentration can be explained in that the dialysis liquid is oversaturated at a high $Ca^{2+}$ ion concentration and $HCO_3^-$ concentration so that the presence of crystallization nuclei, rough surfaces or pressure fluctuations due to the conveying of the dialysis liquid by means of the conveying pump results in the spontaneous precipitation of $CaCO_3$.

It was furthermore now possible to show in laboratory trials that in particular the dialysis liquid filters D1 and D2 are not only the preferred sites for calcification, but also promote the further precipitation themselves on starting calcification:

To verify this, the dialysis liquid filters D1 and D2 were installed and removed on a dialyzer in running operation in accordance with FIG. 2. The conductivity was measured continuously by means of the conductivity measuring cells 20 and 40. As also described above, the sodium and calcium ion concentrations were additionally determined in dialysate samples taken upstream of the dialysis machine D3.

Figure 4:
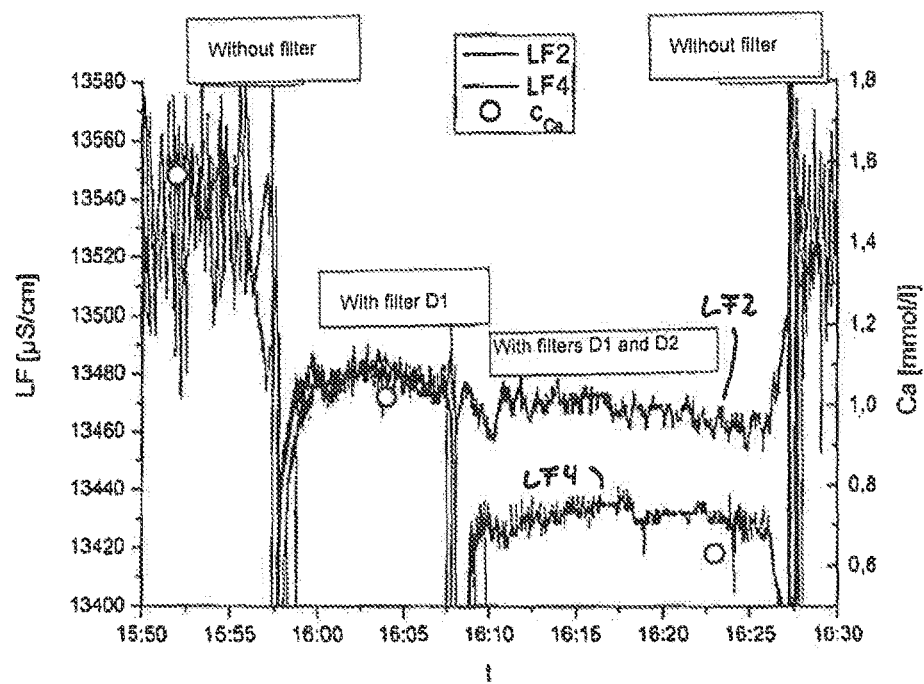
FIG. 4: time curve of the $Ca^{2+}$ ion concentration and of the conductivity on the installation and removal of calcified filters.

As can be seen from FIG. 4, the conductivity fell on installation of the filter D1 at both the sensors 20 (LF2) and 40 (LF4) by approximately 60 μS/cm with respect to the conductivity without a filter. At the same time as the change in conductivity, a fall in the $Ca^{2+}$ ion concentration before the dialysis machine D3 by 0.6 mmol/l could also be found on installation filter D1.

If a calcified filter D2 was additionally installed, the conductivity (LF4) at the sensor 40 fell by a further approximate 50 μS/cm and the $Ca^{2+}$ ion concentration by a further 0.4 mmol/l since the flow path to the sensor 40 now contained two calcified filters D1, D2. The conductivity (LF2) at the conductivity 20 remained constant.

After removal of the two filters D1, D2, the conductivity and the $Ca^{2+}$ on concentration at both measuring cells again reached the original value, as can be seen from FIG. 4.

For clarification, it should be pointed out at this point that the extent of the curve of the value "LF4" in FIG. 4 does not only exist, for instance, in the area "with filters D1 and D2!, but also in the time period before it in which it does not substantially differ from the curve of the parameter "LF2".

It is furthermore pointed out that the measured curves in accordance with FIG. 3 and FIG. 4 are measurements which were obtained in an in vitro structure, with a comparison liquid being circulated instead of blood in the extracorporeal blood circuit. Favorable and unfavorable compositions for the dialysis liquid exist for the occurrence of calcification, in particular with respect to its content of bicarbonate, calcium and acetate. Such combinations were now selected for the trials in which the calcification tended to proceed fast rather than slow. The data and curves shown are therefore not representative for an average dialysis treatment. The measurements shown are rather extreme situations by means of which the effects playing a role within the framework of this invention can be illustrated better.

The values of the $Ca^{2+}$ ion concentration are in good approximation with the change in the $Ca^{2+}$ ion concentration calculated in accordance with the above equation from the change in conductivity. The $Na^+$ ion concentration remained constant in all cases so that changes in the mixture relationship in the generation of the dialysis liquid can be precluded.

The recognition of calcification in the embodiment shown here is based on a change in the conductivity with a mixing ratio which remains constant on the generation of the dialysis liquid, with the change in the conductivity being due to the precipitation of the calcium in the form of calcium carbonate. It must therefore be ensured that both the metering system and the conductivity measurement are not subject to any drifts over the duration of the comparison measurements.

The laboratory experiments were only carried out with compositions of the dialysis liquid which resulted in an oversaturation with $CaCO_3$.

Figure 5:
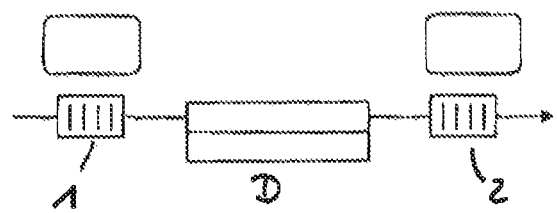
FIG. 5: schematic representation of the calcification monitoring with two conductivity measuring cells per filter.

In an aspect of the invention, an apparatus for the recognition of the calcification of the dialysis liquid filter in the dialyzer or the dialysis machine consists of two conductivity measuring cells which are arranged such that the conductivity of the dialysis liquid or also of a solution serving the decalcification or another measuring solution is measured before and after passage through the filter or the dialysis machine. Such an aspect of the invention is shown in FIG. 5, with the conductivity measuring cells being shown with the reference numerals 1, 2 and the filter with the reference symbol D.

The conductivity measuring cells 1, 2 must be calibrated to one another beforehand. If the influence of the filter D is to be reliably precluded, a bypass 100 must be provided which surrounds the filter D, as can be seen from FIG. 6. The bypass line 100 can be cut off by a valve. The line leading to the filter D can equally be cut off by a valve. Accordingly, depending on the switching of the valves shown in FIG. 6, either the filter D or the bypass line 100 can be flowed through. If a calibration of the conductivity measuring cells 1, 2 should be carried out, the bypass line 100 is flowed through; if the calcification of the filter D should be determined, the bypass line 100 is closed, the filter is flowed through and it is determined by means of the conductivity measuring cells 1, 2 whether a difference can be found in the conductivity values determined upstream and downstream of the filter D.

Figure 7:
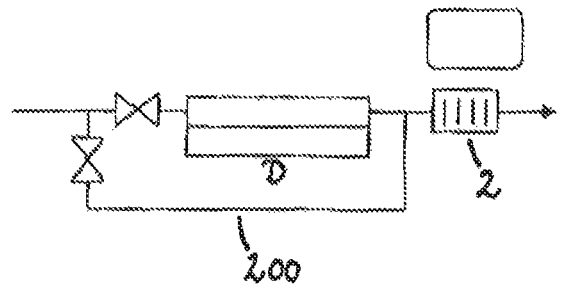
FIG. 7: schematic representation of the calcification monitoring with only one conductivity measuring cell per filter and bypass circuit.

It is also possible alternatively to this to carry out the monitoring of the calcification by only one conductivity measuring cell which is shown with the reference numeral 2 in FIG. 7. This measuring cell is located downstream of the filter D. Furthermore, a bypass line 200 is provided which surrounds the filter D. As can be seen from FIG. 7, the bypass line 200 can likewise be cut off by a valve. The same applies to the line leading to the filter D. If the ion concentration or a parameter representative of this should be determined upstream of the filter D, the bypass line 200 is opened and the conductivity value is detected by means of the conductivity measuring cell 2. If the conductivity should be detected after flowing through the filter D, the line leading to the filter D is opened and the bypass line 200 is closed.

The arrangement in accordance with FIG. 7 provides the advantage that only one conductivity measuring cell with associated electronics is required and, additionally, a calibration of a plurality of measuring cells can also be dispensed with. It must be mentioned as a disadvantage that stabilization times occur here on the switching of the flow paths to measure the conductivity. Furthermore, fairly long times arise in which no dialysis may be possible if the flowing through of the filter D is required for the treatment of the patient.

Figure 8:
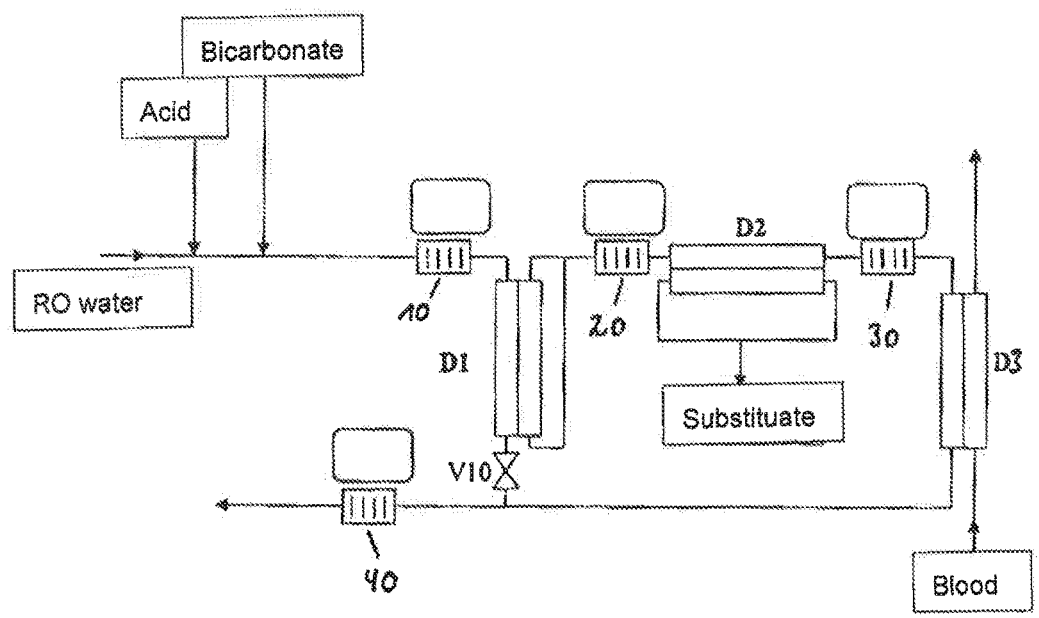
FIG. 8: flow plan of the dialyzer in accordance with FIG. 2 with calcification monitoring of all filters by additional conductivity measuring cells.

FIG. 8 shows the flow scheme in accordance with FIG. 2 with an arrangement of conductivity measuring cells according to the principle described in FIG. 5. The conductivity measuring cells 10, 20 serve the calcification monitoring of the sterile filter D1 and the measuring cells 10, 40 serve the calcification monitoring of the primary side of the sterile filter D1. The conductivity measuring cells 20, 30 serve the monitoring of the sterile filter D2 and the measuring cells 30, 40 serve the monitoring of the dialysis machine D3.

Figure 6:
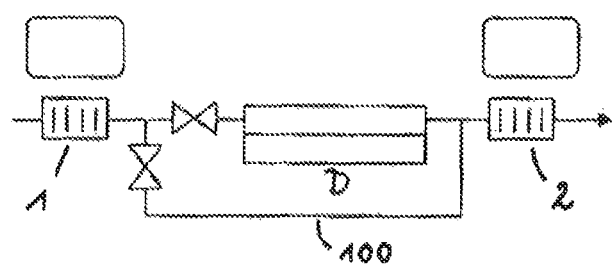
FIG. 6: schematic representation of the calcification monitoring with two conductivity measuring cells per filter, and bypass circuit.
Figure 9:
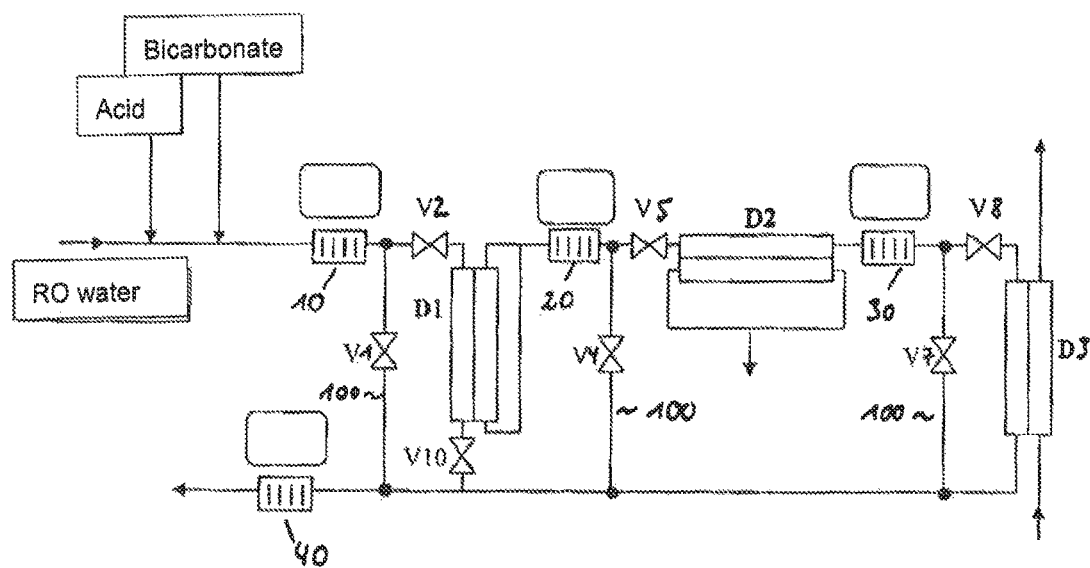
FIG. 9: flow plan of the dialyzer in accordance with FIG. 2 with calcification monitoring of all filters by additional conductivity measuring cells with a calibration possibility.

A flow plan in accordance with FIG. 9 results with a simultaneous calibration possibility in accordance with the principle described in FIG. 6. As can be seen from FIG. 9, bypass lines 100 are respectively provided which are arranged such that each of the conductivity measuring cells 10, 20, 30 can be connected in series with the conductivity measuring cell 40. Accordingly, the calibration of the conductivity measuring cells takes place here by corresponding valve circuits in that the conductivity measuring cells 10, 20 and 30 are connected in series with the conductivity measuring cell 40 while bypassing the respectively subsequently disposed filter D1, D2, D3. This calibration is possible before the start of the dialysis. The valves are switched during the dialysis so that the flow plan in accordance with FIG. 8 results.

Figure 10:
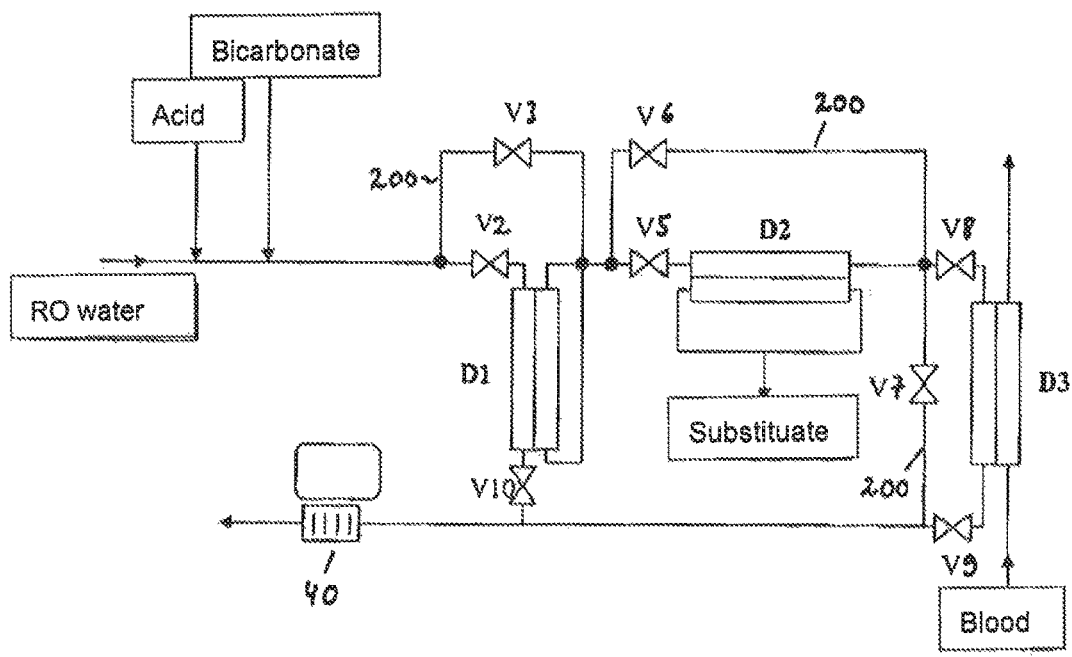
FIG. 10: flow plan of the dialyzer in accordance with FIG. 2 with calcification monitoring of all filters by a conductivity measuring cell and bypass circuits.

As can furthermore be seen from FIG. 10, a monitoring of all filters D1, D2, D3 is also possible with only one conductivity measuring cell 40 by the introduction of bypass lines 200.

The conductivity measuring cell 40 is arranged downstream of the filters D1, D2 and of the dialysis machine D3. For a reference measurement, the bypass lines 200 with the valves V3, V6 and V7 are opened and the valves V2, V5 and V8 in the feed lines to the filters D1, D3 as well as the dialysis machine D3 are closed so that the dialysis liquid flows around the filters D1, D2 and the dialysis machine D3 in the bypass. The valves V10 and V9 are likewise closed.

If the filter D1 should be checked for calcification, the valves V2, V6 and V7 are opened so that the dialysis liquid only flows through the filter D1 from the primary side to the secondary side, whereas a bypass around the filter D2 and the dialysis machine D3 takes place with open valves V6 and V7. All other valves are closed in this case.

If a check of the sterile filter D1 on the primary side should be carried out, the valves V2 and V10 are opened and all other valves are closed. In this case, the dialysis liquid flows through the valve V2, then through the primary side of the sterile filter D1 and then the valve V10 to finally reach the conductivity measuring cell 40.

A check of the calcification state of he sterile filter D2 takes place by opening the valves V3, V5, V7 and by closing all further valves. A check of the dialysis machine D3 takes place with open valves V3, V6, V8, V9, while all further valves are closed.

The table set forth in the following again summarizes which valves are open and closed for the check of which filter or of the dialysis machine and simultaneously shows which conductivity measuring cell can be replaced by the respective arrangements (reference numerals of FIG. 9).

| Test | Open | Closed | Replaced conductivity cell |
|---|---|---|---|
| Reference | V3, V6, V7 | V2, V5, V8, V9, V10 | LF1 (0) |
| D1 | V2, V6, V7 | V3, V5, V8, V9, V10 | LF2 (20) |
| D1, primary side only | V2, V10 | V3, V5, V6, V7, V8, V9 | / |
| D2 | V3, V5, V7 | V2, V6, V8, V9, V10 | LF3 (30) |
| D3 | V3, V6, V8, V9 | V2, V5, V7, V10 | / |

With these theoretically possible switching possibilities, it was not yet taken into account that certain switchings may be less relevant in practice due to the lack of conductivity sensors prescribed for a dialysis treatment and/or of filter stages for the dialysis liquid.

In accordance with the principle described in FIG. 10, a partial reduction of the number of the conductivity measuring cells shown in FIGS. 8 and 9 is also possible.

The conductivity can now be measured continuously for the continuous monitoring of the machine calcification. For this purpose, drifts in the conductivity measurement must possibly be compensated to be able to recognize changes in the conductivity (not the absolute value of the conductivity) with a precision of 0.01 mS/cm.

The procedure of the continuous monitoring of the machine calcification in an arrangement in accordance with FIG. 9 has the following structure:

After a calibration of all conductivity measuring cells 10, 20, 30, 40, the conductivity is measured continuously with them. The monitoring of the filters D1 and D2 takes place by a comparison of the conductivity respectively measured directly before or after the respective filter. A calcification of the filter is present when the conductivity measured after the filter is less than the conductivity measured before the filter. A conclusion on the degree of calcification can be concluded by means of the equation set forth above in the form of a concentration difference. It is important that sufficiently long stabilization times are waited through on changes to the dialysate composition during the treatment.

An initially already present calcification of the filters can be easily recognized using the method in accordance with the invention.

If the dialysis machine D3 should be monitored, it is necessary to eliminate the influence on the patient by stopping the blood pump. At the same time, the flow of the dialysis liquid should be set as high as possible for the fast stabilization of the conductivity at the conductivity measuring cells 30, 40. The evaluation then takes place as described above as for the filters D1 and D2.

If no calibration of the conductivity measuring cells should be carried out via any bypass lines, as applies to FIG. 8, any measuring differences of the individual conductivity measuring cells 10, 20, 30, 40 must be determined at the start of the treatment without the influence of the patient with stable conductivity. The monitoring is then possible as described above while taking account of these initial measuring differences. However, a calcification already present at the start of the treatment cannot be detected precisely in this manner, which represents a disadvantage with respect to the arrangement in accordance with FIG. 9.

As stated above it is also possible that not two conductivity measuring cells are arranged per filter, but only one conductivity measuring cell. In this connection, the one conductivity measuring cell can also be associated with a plurality of filters, as is shown in FIG. 10. In this connection, for each of the filters D1, D2 to be monitored, a measuring cell in accordance with FIG. 7 or FIG. 10 disposed downstream of this filter is required. If no bypasses bypassing the filter should be provided, as is the case, for example, in FIG. 7, and if the composition of the dialysis solution remains constant during the total treatment, an initial value of the conductivity $LF_0$ is determined and stored at the start of the treatment. A fall in the conductivity measured continuously in the further course with respect to the value $LF_0$ then indicates an increase in calcification.

A calcification already present at the start cannot be recognized in this manner.

If the composition of the dialysis liquid changes during the treatment, if the desired sodium value is adjusted by the user during the treatment, for example, then an expected value for the conductivity change can be calculated by means of an empirically determined formula on the basis of the concentration composition and on the conductivity measured at the start. If the measured conductivity falls below the expected conductivity, this is an indication of calcification.

If the filters should each be fitted with bypasses, the full extent of a continuous calcification monitoring and an initial calcification monitoring of all filters can be achieved as described above.

The cause of the presence of calcified filters can be found, for example, in the fact of an insufficient decalcification between treatments. Other causes are the use of already calcified filters or the multiple use of dialysis machines. As stated above, in this connection, there is the risk of the failure of the dialyzer due to lime deposits and, in some cases, the endangering of the patient due to a $Ca^{2+}$ ion concentration of the dialysis liquid which is too low.

As stated above, the calcification recognition can consist of a concentrate mixture being set such that an oversaturated solution is present and that then the conductivity measured values are recorded upstream and downstream of the filter and/or of the dialysis machine to be checked. If bypass circuits are used, a sufficiently long stabilization time must be observed in each case. If the conductivity measured downstream is less than the conductivity measured upstream, calcification can be concluded, with its degree being able to be determined via the aforesaid equation.

If the decalcification process itself should be monitored, the measurement of the conductivity can take place before and after the carrying out of the decalcification cycle or also during the decalcification.

The degree of the calcification can be determined for the filter to be monitored by the method described above (measurement of the conductivity upstream and downstream of the filter) before carrying out the decalcification procedure. After carrying out the decalcification, a renewed determination of the conductivity takes place upstream and downstream of the filter. The filter is completely decalcified when the conductivity upstream and downstream of the filter is identical.

An evaluation of the decalcification is also possible when only one conductivity measuring cell is arranged downstream of the filter. This applies, for example, to the filter D1 and to the conductivity measuring cell 20 in FIG. 2. To carry out the evaluation of the decalcification here, a concentrate mixture may have to be set such that an oversaturated solution is present. Then the measurement of the conductivity is carried out by means of the conductivity measuring cell located downstream and then the decalcification procedure is carried out. Subsequently, the said concentration mixture is again established, the stabilization of the conductivity waited for and the conductivity measured value measured again by means of the downstream measuring cell. A decalcification was at least partly successful when the conductivity after the decalcification is larger than that before the calcification. A conclusion on the degree of the elimination of the calcification can be made by means of the aforesaid equation. This process can be repeated so often until the conductivity before and after the decalcification no longer changes.

It is also possible to asses the progress of decalcification during the decalcification. This procedure is based on the fact that the specific conductivity of $H^+$ ions exceeds that of the others in the dialysis liquid or in the acid used for the decalcification by four to five fold. On the decalcification of a filter by acid, $CaCO_3$ goes into solution while consuming $H^+$ ions, as is shown by the reaction equation given in the following:

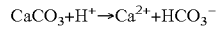

The process of the decalcification can now be monitored by a comparison of the conductivity before and after the filter by an arrangement in accordance with FIG. 6, for example: The acid solution before the filter has a higher conductivity than that after the filter due to the high $H^+$ ion concentration when a consumption of $H^+$ ions has occurred by reaction with $CaCO_3$. The decalcification is ended exactly when the conductivity upstream and downstream of the filter is identical.

A measurement of the conductivity of the dialysate before and after the decalcification is necessary with this process. Alternatively to this, the monitoring can also be carried out by pH sensors during decalcification. As stated above, a consumption of $H^+$ ions takes place during the decalcification and thus a shift of the environment into the alkaline. If the pH no longer changes, the decalcification is ended since then a consumption of the $H^+$ ions by $CaCO_3$ no longer takes place.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of determining the calcification of a dialysis machine having a dialysis liquid filter, other than a dialyzer, for the filtration of a dialysis liquid, the dialysis liquid filter having a primary side and a secondary side, said method comprising the steps of:
    measuring an ion concentration or a parameter representative of an ion concentration, of a measuring solution, with a first measuring cell arranged directly upstream of the dialysis liquid filter;
    bypassing the dialysis liquid filter by opening a bypass line and directing a flow of the measuring solution around the dialysis liquid filter;
    measuring an ion concentration or a parameter representative of an ion concentration, of the measuring solution, after the measuring solution has bypassed the dialysis liquid filter, with a second measuring cell arranged directly downstream of the dialysis liquid filter, such that an influence of the dialysis liquid filter on a difference in a value measured upstream of the dialysis liquid filter and a value measured downstream of the dialysis liquid filter is precluded;
    calibrating the first measuring cell to the second measuring cell based on the ion concentration or parameter of ion concentration measured directly upstream of the dialysis liquid filter and the ion concentration measured directly downstream of the dialysis liquid filter; then
    closing the bypass line;
    flowing the measuring solution from upstream of the dialysis liquid filter to downstream of the dialysis liquid filter, either (1) along the primary side of the dialysis liquid filter or (2) through the dialysis liquid filter from the primary side to the secondary side;
    measuring an ion concentration or a parameter representative of an ion concentration, of the measuring solution, downstream of the dialysis liquid filter with the bypass line closed; and
    determining calcification of the dialysis liquid filter based on a difference between the ion concentration or parameter determined upstream of the dialysis liquid filter and the ion concentration or parameter measured downstream of the dialysis liquid filter with the bypass line closed, wherein a calcification of the dialysis liquid filter is determined to be present when the ion concentration or parameter determined upstream of the dialysis liquid filter is larger than the ion concentration or parameter measured downstream of the dialysis liquid filter with the bypass line closed.

2. The method in accordance with claim 1, wherein the measuring an ion concentration or a parameter representative of an ion concentration comprises measuring a parameter representative of an ion concentration of the measuring solution, and the parameter representative of the ion concentration is a conductivity, a pH, or a parameter determined by an ion-selective electrode or by a spectroscopic method.

3. The method in accordance with claim 1, wherein the measuring an ion concentration or a parameter representative of an ion concentration, of the measuring solution, upstream of the dialysis liquid filter, comprises measuring, conductivity and
   the determining calcification of the dialysis liquid filter is based on a comparison of a conductivity of the measuring solution determined upstream of the dialysis liquid filter and a conductivity of the measuring solution measured downstream of the dialysis liquid filter with the bypass line closed.

4. The method in accordance with claim 3, wherein the measuring the ion concentration or parameter upstream of the dialysis liquid filter comprises measuring a value with the first measuring cell, and the measuring an ion concentration or a parameter downstream of the dialysis liquid filter with the bypass line closed comprises measuring a value with the second measuring cell, and wherein a difference in the values measured by the first and second measuring cells is determined at a first point in time, a difference in the values measured by the first and second measuring cells is determined at a second point in time after the first point in time and during a treatment, and a degree of calcification of the dialysis liquid filter is determined based on a comparison of the difference measured at the first point in time with the difference measured at the second point in time.

5. The method in accordance with claim 1, wherein the dialysis machine comprises a second dialysis liquid filter, wherein the second dialysis liquid filter is arranged downstream of the first-mentioned dialysis liquid filter and upstream of the second measuring cell, the bypass line comprises valves and is configured to direct flow of the measuring solution to bypass the first-mentioned dialysis liquid filter and direct the measuring solution along or through the second dialysis liquid filter, and the method further comprises controlling the valves and flowing the measuring solution such that the flow of measuring solution bypasses the first-mentioned dialysis liquid filter and passes along or through the second dialysis liquid filter.

6. The method in accordance with claim 5, wherein the dialysis machine comprises a third measuring cell arranged between the first-mentioned dialysis liquid filter and the second dialysis liquid filter, the measuring an ion concentration or a parameter comprises sensing a value with the third measuring cell, and the method comprises measuring an ion concentration or a parameter representative of an ion concentration of the measuring solution with the third measuring cell and the second measuring cell while the flow of the measuring solution bypasses the first-mentioned dialysis liquid filter and flows along or through the second dialysis liquid filter.

7. The method in accordance with claim 1, wherein the measuring solution comprises a solution serving decalcification, and the method comprises carrying out a decalcification and making an evaluation of the decalcification after the decalcification or during the decalcification based on the difference between the ion concentration or the parameter representative of the ion concentration measured directly upstream of the dialysis liquid filter and the ion concentration or the parameter of the ion concentration measured directly downstream of the dialysis liquid filter.

8. The method in accordance with claim 1, further comprising carrying out a decalcification and then carrying out an evaluation of the decalcification after the decalcification, wherein the evaluation is based on a comparison of values measured by the first measuring cell and the second measuring cell, before and after the decalcification.

9. The method in accordance with claim 1, wherein the measuring an ion concentration or a parameter representative of an ion concentration with the first measuring cell comprises measuring a $Ca^{2+}$ ion concentration, a parameter representative of a $Ca^{2+}$ ion concentration, an $H^+$ ion concentration, or a parameter representative of an $H^+$ ion concentration.

10. The method according to claim 4, wherein the first point in time is before or at a start of a treatment.

11. The method according to claim 1, wherein the measuring with the second measuring cell while the dialysis liquid filter is bypassed, is carried out before or at the start of a treatment.

12. The method of claim 1, wherein the measuring solution comprises a dialysis liquid or a solution serving decalcification.

13. The method of claim 1, further comprising:
   determining that a calcification of the dialysis liquid filter is present by determining that the ion concentration or parameter determined upstream of the dialysis liquid filter is larger than the ion concentration or parameter measured downstream of the dialysis liquid filter, while the bypass is closed; and
   based on the determination that a calcification of the dialysis liquid filter is present, carrying out a decalcification process to decalcify the dialysis liquid filter.

14. The method of claim 13, wherein the carrying out of the decalcification process comprises flushing the dialysis liquid filter with peracetic acid.

15. A method of determining the calcification of a dialysis machine having a dialysis liquid filter, other than a dialyzer, for the filtration of a dialysis liquid, the dialysis liquid filter having a primary side and a secondary side, the method comprising the steps of:
   measuring the conductivity representative of a $Ca^{2+}$ ion concentration, in a measuring solution, directly upstream of the dialysis liquid filter;
   bypassing the dialysis liquid filter;
   measuring the conductivity representative of a $Ca^{2+}$ ion concentration, in the measuring solution, directly downstream of the dialysis liquid filter, while bypassing the dialysis liquid filter;
   calibrating an upstream sensor and a downstream sensor, to one another, based on the measurements;
   flowing the measuring solution from upstream of the dialysis liquid to downstream of the dialysis liquid filter, either (1) along the primary side of the dialysis liquid filter or (2) through the dialysis liquid filter from the primary side to the secondary side, in a non-bypass mode;

measuring the conductivity representative of a $Ca^{2+}$ ion concentration, in the measuring solution, directly upstream of the dialysis liquid filter;

measuring the conductivity representative of a $Ca^{2+}$ ion concentration, in the measuring solution, directly downstream of the dialysis liquid filter, in the non-bypass mode; and determining whether there is calcification of the dialysis liquid filter based on the measured conductivities, wherein a calcification of the dialysis liquid filter is determined to be present when the conductivity measured directly upstream of the dialysis liquid filter is larger than the conductivity measured directly downstream of the dialysis liquid filter, in the non-bypass mode.

16. The method in accordance with claim 15, further comprising:

determining a difference between the conductivity measured directly upstream of the dialysis filter and the conductivity measured directly downstream of the dialysis liquid filter, in the non-bypass mode, to determine a conductivity difference based on the filter;

determining a difference between the conductivity measured directly upstream of the dialysis filter and the conductivity measured directly downstream of the dialysis liquid filter, while bypassing the dialysis liquid filter, to determine a bypass difference; and comparing the bypass difference to the conductivity difference based on the filter, to form a comparison.

17. The method in accordance with claim 15, wherein:

the measuring of the conductivity representative of a $Ca^{2+}$ ion concentration, in the measuring solution, directly upstream of the dialysis liquid filter, is carried out by an upstream conductivity measuring cell;

the measuring of the conductivity representative of a $Ca^{2+}$ ion concentration, in the measuring solution, directly downstream of the dialysis liquid filter, is carried out by a downstream conductivity measuring cell; and the method further comprises calibrating the upstream and downstream conductivity measuring cells based on the comparison.

18. The method of claim 15, further comprising:

determining that the conductivity representative of a $Ca^{2+}$ ion concentration, in the measuring solution, measured upstream of the dialysis liquid filter is larger than the conductivity representative of a $Ca^{2+}$ ion concentration, in the measuring solution, measured downstream of the dialysis liquid filter, in the non-bypass mode, and concluding that a calcification of the dialysis liquid filter is present; and based on the conclusion that a calcification of the dialysis liquid filter is present, carrying out a decalcification process to decalcify the dialysis liquid filter.

19. The method of claim 18, wherein the carrying out of the decalcification process comprises flushing the dialysis liquid filter with peracetic acid.

* * * * *